United States Patent [19]

Mita et al.

[11] Patent Number: 4,740,383
[45] Date of Patent: Apr. 26, 1988

[54] METHOD OF CHECKING THE DEGREE OF PLASMA TREATMENT

[75] Inventors: Fumio Mita; Kuniharu Kitagawa, both of Tokyo; Takashi Arakawa; Setsuo Simizu, both of Kanagawa, all of Japan

[73] Assignee: Fuji Photo Film Co., Ltd., Kanagawa, Japan

[21] Appl. No.: 71,238

[22] Filed: Jul. 9, 1987

[30] Foreign Application Priority Data

Jul. 9, 1986 [JP] Japan ................................. 61-159548

[51] Int. Cl.$^4$ .............................................. B05D 3/02
[52] U.S. Cl. ...................................... 427/10; 427/38; 427/45.1
[58] Field of Search .......................... 427/10, 38, 45.1

Primary Examiner—Bernard D. Pianalto
Attorney, Agent, or Firm—Sughrue, Mion, Zinn, Macpeak & Seas

[57] ABSTRACT

A method for checking the degree of plasma treatment of an article. The method comprises depositing a substance able to change color as a result of plasma treatment on a carrier, the carrier having pores having an average pore size of 0.2–3 μm, placing the carrier having said substance deposited thereon near the surface of the article, subjecting the substance carrying carrier and the article to plasma treatment, and evaluating the color change that has occurred in the substance.

11 Claims, No Drawings

METHOD OF CHECKING THE DEGREE OF PLASMA TREATMENT

DESCRIPTION

The present invention relates to a method of checking the degree of plasma treatment applied to the surface of various articles. In particular, the present invention relates to a method by which the degree of plasma treatment applied to a article can be checked in a correct and simple manner.

BACKGROUND OF THE INVENTION

In response to the need of society at large for the conservation of natural resources and energies, various methods have been studied by car manufacturers to reduce the fuel consumption of running automobiles. One of the approaches under current review is to make automotive parts from materials other than metal or steel. In practice, attempts are being made to minimize the weight of a car by replacing metal with lighter materials such as high-tensile steel, aluminum and plastics in as many parts as possible. Car exterior parts such as bumpers have heretofore been made of metal materials which are painted to provide corrosion resistance and good appearance. Plastic parts are corrosion-resistant by themselves, but as such their appearance is not as good as the appearance of painted metal parts. To solve this problem, coloring of plastic parts is currently under review, but because of the inherently low thermal deformation temperature of plastics compared with metal, the latitude for the selection of suitable coloring paints is fairly limited.

Metals which generally have high surface energies are labile in their elemental form and become stable when an energy-lowering oxide film forms on the surface as a result of adsorption of aerial moisture or oxygen or acidic gases. On the other hand, plastics having low surface energies have poor paint receptivity. Among various plastics known today, polypropylene is characterized by particularly low paint receptivity because it is highly crystalline, has a large angle of contact with water, has a low surface energy and is nonpolar. Therefore, in order to provide plastics with improved adhesion to paint coating, a special surface treatment is necessary before paint application.

A number of methods have been proposed for effecting such preliminary treatment of plastics and they include primer application, plasma treatment, irradiation with ultraviolet rays, chromate treatment, flame treatment, electric discharging, and exposure to radiation. Of these methods, only the primer application has been commercialized. however, there are not many manufacturers of suitable primer paints and, in addition, the production cost and sales prices of such primer paints are still high. In order to overcome these disadvantages, studies have been conducted into replacing the method of primer application by plasma treatment. As shown in Unexamined published Japanese Patent Application Nos. 147432/1983 and 147433/1983, active efforts are underway principally for the purpose of modifying the surface of polyolefinic resins such as polyethylene and polypropylene. Achieving the plasma treatment to a surface of the plastic material is also shown in "Plastics Engineering", page 41, (October, 1985) and in "Journal of Applied Polymer Science" Vol. 11, page 1461, (1967).

Plasma treatment is a dry method that employs either oxygen (to effect surface oxidation) or an inert gas as a plasma source. Unlike the method of primer application, plasma treatment is capable of preliminary treatment of plastic articles at low cost. However, this method requires the operator to check whether satisfactory plasma treatment has been achieved. Conventionally, the checking has been accomplished by performing, after paint application, a peel test (or adhesion test) (JIS K 6829) on the paint or a surface tension test on the surface of the plastic article (in which the change in its surface tension with a wetting reagent is determined). However, these methods have the following problems: because of the complexity of the checking procedures, samples have to be extracted from each lot of the products or the production line has to be stopped for each checking; even if defective products are found, the lot from which they have been sampled is already in the stage of subsequent steps; the results of checking are not quantitative; and great skill is required for ensuring reliable checking.

With a view to eliminating these problems, it has been proposed to apply a substance that will change properties or color upon plasma treatment to a plastic article and to check the degree to which the article has been subjected to plasma treatment by evaluating the degree by which the substance has changed color as a result of plasma treatment. In this method, a phthalocyanine dye may be used as the substance that changes color upon plasma treatment; when subjected to treatment with an oxygen plasma in a treatment bath, the dye is excited to produce a pink color, which is retained for about 10 minutes even after it is recovered from the bath and gradually turns red purple, then blue purple, and finally blue. Therefore, by observing such changes in color, the degree of plasma treatment applied to the plastic article can be checked.

The method described above has several defects. For one thing, if a substance that changes in properties or color upon plasma treatment is simply attached to the plastic article, it sometimes evaporates from the surface of the article during plasma treatment and fails to provide satisfactory results in subsequent checking. Secondly, even if the plastic article has good dyeability, with the dye being deposited on it in a sufficient thickness to avoid its loss due to evaporation, the actual change that has occurred in the dye cannot be fully checked if its coat has a smooth surface. No matter how much dye is deposited on the surface of the article, it is only the dye present in the surface of the dye layer that changes color upon plasma treatment and the color of the unreacted dye in the deeper area of the dye layer can be seen through its surface, which makes it practically impossible to selectively observe the color change that has occurred in the surface layer of dye.

SUMMARY OF THE INVENTION

An object of the present invention is to provide an improved method for checking the degree of plasma treatment of an article.

The present invention provides a method for checking the degree of plasma treatment of an article comprising depositing a substance able to change color as a result of plasma treatment on a carrier, the carrier having pores having an average pore size of 0.2-3 μm, placing the carrier having said substance deposited thereon near the surface of the article, subjecting the substance carrying carrier and the article to plasma treatment, and evaluating the color change that has occurred in the substance.

DETAILED DESCRIPTION OF THE INVENTION

An example of the article to be subjected to plasma treatment in the method of the present invention is a plastic article made of such a material as a thermosetting plastic, a heat-softening plastic or a natural plastic. Specific examples of the plastic article include shaped articles, painted articles and shaped composites (e.g. by lamination) of plastics such as phenolic resins, melamine resins, epoxy resins, alkyd resins, unsaturated polyester resins, polyethylene, polypropylene, polystyrene, polyacrylic acid, polyurethane, polycarbonate, polyamide, polysulfone, silicone resins, and cellulosic plastics. As described in connection with the prior art, these articles are used in practice as exterior parts, such as those of machines and apparatus (e.g. automotive parts), buildings, miscellaneous daily necessities, and various other products. As discussed above, these exterior parts are to be colored by painting. Paints that can be applied to plastic articles include water-based paints, oil-based paints and emulsion-type paints, and they may be classified by composition into such types as synthetic resin based paints, cellulosic derivative based paints, and alcohol-based paints.

The present invention provides a method for checking the degree of plasma treatment of a variety of articles such as the plastic articles mentioned above. In this method, a substance that will change color as a result of plasma treatment is deposited on a carrier material, preferably plastic, having a pore size of 0.2–3 μm. The substance carrying carrier is placed near the surface of the article and subjected to plasma treatment together with the article. After plasma treatment, the change in substance color is observed as an indicator of the amount of plasma treatment received by the article.

Porous plastic carriers having a pore size of 0.2–3 μm are available as commercial products such as cellulose membrane filters, nylon membrane filters, polypropylene membrane filters, polyethylene membrane filters, and polysulfone membrane filters. The substance that changes color upon plasma treatment is deposited in the pores in these porous carriers.

The porous plastic carrier is in a sheet or film form, with its thickness being in a range of 120 μm to 180 μm. The plastic carrier is in the form of porous or skeletonized body having a plurality of small pores. The pores are formed in reticular state in the plastic carrier. The diameter or size, at a surface portion of the carrier, of the pores (which is not a depth of the pores) is in a range of 0.2 μm to 3 μm. It is difficult to produce porous material having pores with their diameter less than 0.2 μm. On the other hand, on a porous material having pores with their diameter more than 3 μm, it is impossible to form pigment layer having a uniform hue, but pigment layer is formed such that the pigment layer has spots of hue thereon.

For example, applicable in the present invention is a porous carrier sheet in which average pore size is 0.45 μm, and distribution of the pore size is measured by a method provided by ASTM F-316 to prove that 75% of the pores have diameters less than 0.5 μm and the remaining pores have diameters in a range of 0.5 μm to 0.8 μm.

The porous carrier sheet is formed as follows: A solution of the material for the above-described porous carrier, such as cellulose membrane filters, etc. and a non-solvent are mixed such that phases are separated from each other. In this state, the solvent in the solution of the material for the carrier is evaporated to dryness, with the non-solvent being removed by evaporation or extraction, as a result of which a film or sheet shaped carrier having plural small pores is formed.

Examples of the substance that will change color upon plasma treatment include:

(1) phthalocyanine-based reactive dyes, such as copper(29H,31H-phthalocyanine-tri-sulfonato-(2)-$N^{29},N^{30},N^{31},N^{32}$)-trisodium, represented by the formula

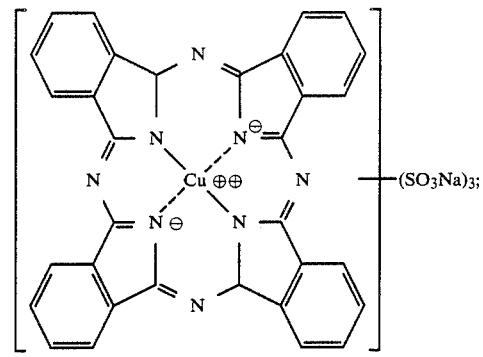

(2) fluoran-based dyes, such as disodium-2-(6-hydroxy-2,4,5,7-tetraiodo-3-oxo-3H-xanthen-9-yl)benzonate, represented by the formula

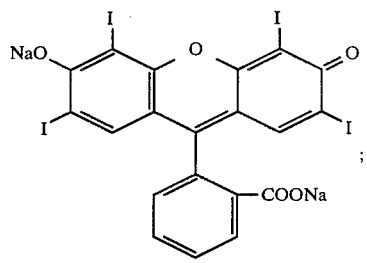

(3) azobenzene-based dyes, such as Methyl Red, represented by the formula

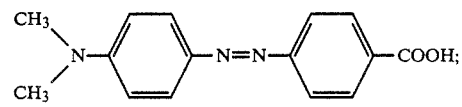

(4) triphenylmethane-based dyes, such as 3',5',3'',5''-tetrabromo-m-cresol-sulfonphthalein (Bromo cresol green), represented by the formula

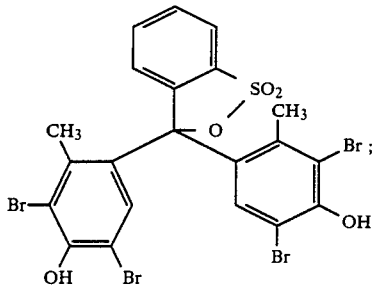

(5) stilbenze-based dyes, such as 4-dimethylamino-2',4'-dinitrostilbene; and (6) indophenol-based dyes, such as 2,6-dichloro indophenol, represented by the formula

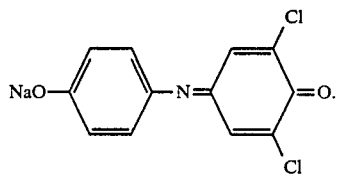

When subjected to plasma treatment, phthalocyanine-based reactive dyes produce a pink color which returns to the original color upon standing, and therefore, such dyes can be used over and over again. Triphenylmethane-based dyes and stilbene-based dyes undergo an irreversible color change upon plasma treatment, the former from blue to yellow, and the latter from white to yellow.

The substance that changes color or its physical property upon plasma treatment can be deposited in the pores of the porous surface of the carrier by any suitable method such as dissolving the dye in a solvent and applying the solution to the carrier, or immersing the carrier in the solution. In the case where the solution of the dye substance is applied to the surface of the porous carrier, the amount of the dye solution applied is about 60 g/m². In both cases, the dye solution enters pores, and is deposited in all the portions of the porous carrier. That is, the dye solution is deposited not only at the surface of the porous carrier but also at the inside wall of the pores. The deposit amount of the dye solution is selected so that the dye solution will be deposited on the inside wall of the pores but the pores will not be filled completely full with the dye solution. The so-treated carrier is then cut to a desired size.

The dye-containing carrier is placed near the plastic article to be subjected to plasma treatment. As plasma treatment on the article proceeds, the dye-containing carrier changes color and the degree of effective plasma treatment can be checked by examining the amount of color change or physical property change which has occured.

Since the dye solution layer is formed in the porous carrier, the dye solution amount per a unit area of the carrier is increased so that the degree of the color change of the dye is emphasized. The color change of the dye due to plasma treatment is occurred only at the surface portion of the dye solution layer, but is occured at all the portions in the carrier to a bottom or reverse surface of the carrier in a carrier thickness direction. In other words, the effect of the plasma treatment is obtained even at the bottom positioned pores.

In order to examine the degree of the color change of the dye, it is sufficient to examine the color of the dye by comparing it with a standard sample for indicating several grades of color change, with the naked eye. Furthermore, the degree of the color change of the dye may be measured by a color densitometer such as Macbeth densitometer.

According to the present invention, a carrier in the form of a porous plastic material on which a substance that will change color upon plasma treatment has been deposited is placed near the surface of an article to be subjected to plasma treatment. The deposited substance will not vaporize during the course of plasma treatment and in comparison with the case in which the substance is deposited on a smooth-surfaced plastic article. Further, the carrier used in the present invention will be subjected to plasma treatment over a large area, and experiences a color change that is distinct enough to provide for easy checking of the degree to which plasma treatment has occurred.

The present invention is hereunder described in greater detail by means of examples, but is not limited thereby.

EXAMPLE 1

Two grams of a fluoran dye were dissolved in 1,000 ml of chloroform to prepare a dye solution. This solution was dip-coated on two materials which are to be used as carriers in checking the degree of plasma treatment. One carrier material (hereafter Carrier A) was a cellulosic "Microfilter" with an average pore size of 0.45 μm* (tradename of Fuji Photo Film Co., Ltd.). The other carrier material (hereafter Carrier B), which was intended for making a comparative sample, was a polyester film** 100 μm thick (product of Fuji Photo Film Co., Ltd.)

*A membrane filter with an asymmetric structure that was prepared from a solution of regenerated cellulose in a mixed solvent by flow casting.
**A smooth-surfaced film of polyethylene terephthalate formed by melt filming.

After drying, a 20 mm × 50 mm sample was cut from each of the carrier materials and subjected to plasma treatment under the following conditions:

Processing conditions

Apparatus: microwave plasma treatment apparatus, Model TMW-7407 of Toshiba Corporation
Pressure: 1 torr
Oxygen flow rate: 200 cc/min
Time: 30 sec
Power: 1 kW.

After the plasma treatment, the treated samples were taken out of the apparatus and the color was checked against corresponding substance containing carrier materials which had not been plasma treated. The color of the treated Carrier A sample, prepared from the cellulosic "Microfilter", had completely turned from blue to white, whereas only a slight color change had occurred in the treated comparative Carrier B. This result amply shows the effectiveness of the method of the present invention.

EXAMPLES 2-4 AND COMPARATIVE EXAMPLE

Two grams of a pyrazolone/oxonole based dye was dissolved in 1,000 ml of chloroform to prepare a dye solution. The procedures of Example 1 were repeated except that the material for the carrier to be used in checking the degree of plasma treatment was changed to those listed in Table 1. The results of plasma treatment conducted on these carriers are also shown in Table 1.

TABLE 1

| Run No. | Carrier (film) | Color change after plasma treatment |
| --- | --- | --- |
| Example 2 | mixed cellulose ester filter*** | marked change |
| Example 3 | polypropylene filter**** | marked change |
| Example 4 | filter paper | some change |
| Comparative Example | triacetyl cellulose film***** | no change |

***A membrane filter having an asymmetric molecular structure that was produced by flow-casting a mixture of nitrocellulose and acetyl cellulose dissolved in a solvent system containing a poor solvent.
****A filter with micro pores that was produced by sintering polypropylene particles.
*****A smooth-surfaced film that was produced by flow-casting a solution of triacetyl cellulose in methylene chloride.

It is clearly evident from the data in Table 1 that the method of the present invention was also effective with the above-described samples of the Examples 2 to 4.

EXAMPLE 5

Two grams of an indophenol dye was dissolved in 1,000 ml of methanol to make a dye solution. The dye solution was applied to two carrier materials, to form dye layers having the same optical density with each other; the materials were a cellulosic "Microfilter" with an average pore size of 0.45 μm (tradename of Fuji Photo Film Co., Ltd.) and filter paper "Filter Paper for Quantitative Assay No. 2" (tradename of Toyo Roshi Kaisha Ltd.). After drying, each carrier material was cut into a number of samples each having a size of 20×50 mm, and the so prepared carrier samples were subjected to plasma treatment under the following conditions:

Processing conditions

Apparatus: microwave plasma treatment apparatus, Model TMW-7407 of Toshiba Corporation
Pressure: 1 torr
Oxygen flow rate: 200 cc/min
Time: 0, 4, 16, 30 and 60 sec
Power: 1 kW.

After the plasma treatment, the carrier samples were taken out of the apparatus and their surface color reflection densities were measured with a Macbeth reflection densitometer, RD-914 (tradename of Macbeth Instrument Corporation). The results are shown in Table 2.

TABLE 2

| Time (sec) | Microfilter | Filter paper |
| --- | --- | --- |
| 0 | 0.36 | 0.36 |
| 4 | 0.25 | 0.34 |
| 16 | 0.16 | 0.33 |
| 30 | 0.11 | 0.33 |
| 60 | 0.04 | 0.30 |

The data in Table 2 shows that the carrier samples made from "micro filter" experienced a much greater change in color density than those made from filter paper.

EXAMPLE 6

Two grams of a bromocresol green was dissolved in 1,000 ml of methanol to make a dye solution. The dye solution was applied to two carriers, to form dye layers having the same optical density to each other; the carriers were a nylon micro filter "PA-6D" (tradename of Enka Co., Ltd.) and filter paper "Filter Paper for Quantitative Assay No. 2" (tradename of Toyo Roshi Kaisha Ltd.). Samples of each carrier were subjected to plasma treatment under the same conditions as used in Example 5 and their reflection densities were measured as in Example 5. The results are shown in Table 3.

TABLE 3

| Time (sec) | Nylon micro filter | Filter paper |
| --- | --- | --- |
| 0 | 0.50 | 0.51 |
| 4 | 0.38 | 0.50 |
| 16 | 0.22 | 0.43 |
| 30 | 0.10 | 0.46 |
| 60 | 0.02 | 0.45 |

The data in Table 3 shows that compared with the samples formed by a carrier made from filter paper, those using a carrier made from a material having a very large surface area such as micro filter experienced a significant change in color as a result of plasma treatment conducted for a fairly short period of time.

According to the present invention, the degree of plasma treatment conducted on an article can be checked quantitatively in a very simple manner. Therefore, the present invention attains the following advantages: on-site checking of individual products can be accomplished in a reliable way without stopping the production line; the cost of subsequent coloring can be significantly reduced; and optimum conditions for plasma treatment can be determined by using the method of the present invention.

What is claimed is:

1. A method of checking the degree of plasma treatment of an article, comprising depositing a substance on a carrier, said substance being able to change color as a result of plasma treatment, said carrier having pores having an average pore size of 0.2–3 μm, placing the carrier having said substance deposited thereon near the surface of the article, subjecting the substance carrying carrier and the article to plasma treament, and evaluating the color change that has occurred in said substance.

2. A method as in claim 1, wherein the carrier is comprised of a plastic material.

3. A method as in claim 2, wherein the carrier is a cellulose filter, a nylon membrane filter, a polypropylene membrane filter, polyethylene membrane filter, or a polysulfone membrane filter.

4. A method as in claim 1, wherein the substance that changes color upon plasma treatment is selected from the group consisting of phthalocyanine-based reactive dyes, fluoran-based dyes, azobenzene-based dyes, triphenylmethane-based dyes, and stilbene-based dyes.

5. A method of evaluating the degree of plasma treatment of a substrate, comprising:
   (a) depositing a substance capable of changing color as a result of plasma treatment onto a porous plastic material having a pore size of about 0.2 to about 3 μm;
   (b) placing said porous plastic material having said substance thereon near the surface of a substrate;

(c) subjecting said substrate and said porous plastic material having said substance thereon to plasma treatment; and (d) evaluating the color change in said substance as a result of said plasma treatment.

6. A method of evaluating the degree of plasma treatment as claimed in claim 5, wherein said substrate is a plastic substrate.

7. A method of evaluating the degree of plasma treatment as claimed in claim 6, wherein said plastic substrate is selected from the group consisting of shaped plastic articles, painted plastic articles and shaped plastic composites.

8. A method of evaluating the degree of plasma treatment as claimed in claim 7, wherein said plastic is selected from the group consisting of phenolic resins, melamine resins, epoxy resins, alkyd resins, unsaturated polyester resins, polyethylene, polypropylene, polystrene, polyacrylic acid, polyurethane, polycarbonate, polyamide, polysulfone, silicone resins, and cellulosic plastics.

9. A method of evaluating the degree of plasma treatment as claimed in claim 5, wherein said porous plastic material is selected from the group consisting of cellulose membrane filters, nylon membrane filters, polypropylene membrane filters, polyethylene membrane filters, and polysulfone membrane filters.

10. A method of evaluating the degree of plasma treatment as claimed in claim 5, wherein said substance capable of changing color as a result of plasma treatment is selected from the group consisting of phthalocyanine-based dyes, fluoran-based dyes, azovenzene-based dyes, triphenylmethane-based dyes, stilbene-based dyes, and indophenol-based dyes.

11. A method of evaluating the degree of plasma treatment as claimed in claim 5, wherein said placing comprises locating said porous plastic material having said substance thereon and said substrate in a microwave plasma treatment apparatus, and said plasma treatment is conducted in said microwave plasma treatment apparatus.

* * * * *